United States Patent [19]
Tustin et al.

[11] Patent Number: 5,900,505
[45] Date of Patent: May 4, 1999

[54] HETEROGENEOUS VAPOR PHASE CARBONYLATION PROCESS

[75] Inventors: Gerald Charles Tustin; Joseph Robert Zoeller; Horace Lawrence Browning, Jr.; Andy Hugh Singleton, all of Kingsport, Tenn.

[73] Assignee: Eastman Chemical Company, Kingsport, Tenn.

[21] Appl. No.: 09/010,776

[22] Filed: Jan. 22, 1998

Related U.S. Application Data

[60] Provisional application No. 60/037,186, Feb. 4, 1997.

[51] Int. Cl.$^6$ .......................... C07C 51/12; C07C 51/10; C07C 67/36
[52] U.S. Cl. ...................... 562/519; 560/232; 562/517
[58] Field of Search .............................. 560/232; 562/517, 562/519

[56] References Cited

U.S. PATENT DOCUMENTS

| | | |
|---|---|---|
| 3,689,533 | 9/1972 | Schultz . |
| 3,717,670 | 2/1973 | Schultz . |
| 3,772,380 | 11/1973 | Paulik et al. . |
| 4,417,077 | 11/1983 | Drago et al. . |
| 4,612,387 | 9/1986 | Feitler . |
| 4,776,987 | 10/1988 | Luft et al. . |
| 4,845,163 | 7/1989 | Panster et al. . |
| 4,918,218 | 4/1990 | Mueller et al. . |
| 5,144,068 | 9/1992 | Smith et al. . |
| 5,185,462 | 2/1993 | Evans et al. . |
| 5,218,140 | 6/1993 | Wegman . |
| 5,258,549 | 11/1993 | Pimblett . |
| 5,488,143 | 1/1996 | Uhm et al. . |
| 5,510,524 | 4/1996 | Garland et al. . |

FOREIGN PATENT DOCUMENTS

| | | |
|---|---|---|
| 0 120 631 A1 | 10/1984 | European Pat. Off. . |
| 0 130 058 A1 | 1/1985 | European Pat. Off. . |
| 0 461 802 A2 | 12/1991 | European Pat. Off. . |
| 0 596 632 A1 | 5/1994 | European Pat. Off. . |
| 0 752 406 | 1/1997 | European Pat. Off. . |
| 0 759 419 A1 | 2/1997 | European Pat. Off. . |
| 296 275 | 11/1991 | Germany . |

OTHER PUBLICATIONS

Maneck et al, Catalysis Today, 3, (1988), 421–429.
Gelin et al, Pure & Appl. Chem., vol. 60, No. 8, (1988), 1315–1320.
Krzywicki et al, Journal of Molecular Catalysis, 6, (1979), 431–440.
Fujimoto et al, Chemistry Letters, (1987), 895–898.
Fujimoto et al, Journal of Catalysis, 133, (1992), 370–382.
Liu et al, Ind. Eng. Chem. Res., 33, (1994), 488–492.
Howard et al, Catalysis Today, 18, (1993) 325–254.
Fujimoto et al, Catalysis Letters, 2, (1989) 145–148.
Gates et al, Journal of Molecular Catalysis, 3 (1977/78) 1–9.

*Primary Examiner*—Samuel Barts
*Assistant Examiner*—Rosalynd Keys
*Attorney, Agent, or Firm*—Michael J. Blake; Matthew W. Smith; Harry J. Gwinnell

[57] ABSTRACT

Disclosed is a process wherein a mixture of methanol or a methanol source, a halide and carbon monoxide are contacted in the vapor phase with a supported catalyst comprising iridium and at least one second metal selected from ruthenium, molybdenum, tungsten, palladium, platinum and rhenium deposited on a catalyst support material.

16 Claims, No Drawings

HETEROGENEOUS VAPOR PHASE CARBONYLATION PROCESS

REFERENCE TO RELATED APPLICATION

This application claims the benefit of U.S. Provisional Application No. 60/037,186, filed February 04, 1997.

FIELD OF THE INVENTION

This invention pertains to a novel process for the production of acetic acid, methyl acetate or a mixture thereof by the carbonylation of methanol or methanol source. More specifically, this invention pertains to a process wherein a mixture of methanol or a methanol source, a halide and carbon monoxide are contacted in the vapor phase with a supported catalyst comprising iridium and at least one second metal selected from ruthenium, molybdenum, tungsten, palladium, platinum and rhenium deposited on a catalyst support material. The novel process provides a number of advantages, including improved production rates, with respect to known processes for the manufacture of acetic acid, methyl acetate or a mixture thereof from methanol.

BACKGROUND OF THE INVENTION

Processes for the manufacture of acetic acid from methanol by carbonylation are operated extensively throughout the world. A thorough review of these commercial processes and other approaches to accomplishing the formation of acetyls from single carbon sources is described by Howard et al. in *Catalysis Today,* 18 (1993) 325–254. All commercial processes for the preparation of acetic acid by the carbonylation of methanol presently are performed in the liquid phase using homogeneous catalyst systems comprising a Group VIII metal and iodine or an iodine-containing compound such as hydrogen iodide and/or methyl iodide. Rhodium is the most common Group VIII metal catalyst and methyl iodide is the most common promoter. These reactions are conducted in the presence of water to prevent precipitation of the catalyst. U.S. Pat. No. 5,144,068 describes the inclusion of lithium in the catalyst system which allows the use of less water in the Rh-I homogeneous process. Iridium also is an active catalyst for methanol carbonylation reactions but normally provides reaction rates lower than those offered by rhodium catalysts when used under otherwise similar conditions. U.S. Pat. No. 5,510,524 teaches that the addition of rhenium improves the rate and stability of both the Ir-I and Rh-I homogeneous catalyst systems. European Patent Application EP 0 752 406 A1 teaches that ruthenium, osmium, rhenium, zinc, cadmium, mercury, gallium, indium, or tungsten improve the rate and stability of the liquid phase Ir-I catalyst system. Generally, the homogeneous carbonylation processes presently being used to prepare acetic acid provide relatively high production rates and selectivity. However, heterogeneous catalysts offer the potential advantages of easier product separation, lower cost materials of construction, facile recycle and even higher rates.

Schultz, in U.S. Pat. No. 3,689,533, describes the use of supported rhodium as a heterogeneous catalyst for the carbonylation of alcohols to carboxylic acids in the vapor phase in the presence of a halide promoter. In U.S. Pat. No. 3,717,670, Schultz describes a similar supported rhodium catalyst in combination with promoters selected from Groups IB, IIIB, IVB, VB, VIB, VIII, (current notations: 11, 3, 4, 5, 6 and 8–10 respectively) lanthanide and actinide elements of the Periodic Table. Uhm, in U.S. Pat. No. 5,488,143, describes the use of alkali, alkaline earth or transition metals as promoters for supported rhodium for the halide-promoted, vapor phase methanol carbonylation reaction. Pimblett, in U.S. Pat. No. 5,258,549, teaches that the combination of rhodium and nickel on a carbon support is more active than either metal by itself.

In addition to the use of iridium as a homogeneous alcohol carbonylation catalyst, Paulik et al., in U.S. Pat. No. 3,772,380, describe the use of iridium on an inert support as a catalyst in the vapor phase, halogen-promoted, heterogeneous alcohol carbonylation process. European Patent Applications EP 0 120 631 A1 and EP 0 461 802 A2 describe the use of special carbons as supports for single transition metal component carbonylation catalysts.

European Patent Application EP 0 759 419 A1, published Feb. 26, 1997, after the filing date of Provisional Application No. 60/037,186 cited above, pertains to a process for the carbonylation of an alcohol and/or a reactive derivative thereof. EP 0 759 419 A1 discloses a carbonylation process comprising a first carbonylation reactor wherein an alcohol is carbonylated in the liquid phase in the presence of a homogeneous catalyst system and the off gas from this first reactor is then mixed with additional alcohol and fed to a second reactor containing a supported catalyst. The homogeneous catalyst system utilized in the first reactor comprises a halogen component and a Group VIII metal selected from rhodium and iridium. When the Group VIII metal is iridium, the homogeneous catalyst system also may contain an optional co-promoter selected from the group consisting of ruthenium, osmium, rhenium, cadmium, mercury, zinc, indium and gallium. The supported catalyst employed in the second reactor comprises a Group VIII metal selected from the group consisting of iridium, rhodium and nickel, and an optional metal promoter on a carbon support. The optional metal promoter may be iron, nickel, lithium and cobalt. In the process exemplified in EP 0 759 419 A1, the conditions within the second carbonylation reactor zone are such that mixed vapor and liquid phases are present in the second reactor. The presence of a liquid phase component in the second reactor inevitably leads to leaching of the active metals from the supported catalyst which, in turn, results in a substantial decrease in the activity of the catalyst.

The literature contains several reports of the use of rhodium-containing zeolites as vapor phase alcohol carbonylation catalysts at one bar pressure in the presence of halide promoters. The lead references on this type of catalyst are presented by Maneck et al. in *Catalysis Today,* 3 (1988), 421–429. Gelin et al., in *Pure & Appl. Chem.,* Vol 60, No. 8, (1988) 1315–1320, provide examples of the use of rhodium or iridium contained in zeolite as catalysts for the vapor phase carbonylation of methanol in the presence of halide promoter. Krzywicki et al., in *Journal of Molecular Catalysis,* 6 (1979) 431–440, describe the use of silica, alumina, silica-alumina and titanium dioxide as supports for rhodium in the halide-promoted vapor phase carbonylation of methanol, but these supports are generally not at efficient as carbon. Luft et al., in U.S. Pat. No. 4,776,987 and in related disclosures, describe the use of chelating ligands chemically attached to various supports as a means to attach Group VIII metals to a heterogeneous catalyst for the halide-promoted vapor phase carbonylation of ethers or esters to carboxylic anhydrides. Evans et al., in U.S. Pat. No. 5,185,462, describe heterogeneous catalysts for halide-promoted vapor phase methanol carbonylation based on noble metals attached to nitrogen or phosphorus ligands attached to an oxide support. Panster et al., in U.S. Pat. No. 4,845,163, describe the use of rhodium-containing organopolysiloxane-ammonium compounds as heterogeneous catalysts for the halide-promoted liquid phase carbonylation of alcohols. Drago et al., in U.S. Pat. No. 4,417,077, describe the use of anion exchange resins bonded to anionic forms of a single transition metal as catalysts for a number of carbonylation reactions including the halide-promoted carbonylation of methanol. Although supported ligands and anion exchange resins may be of some use for immobilizing metals in liquid phase carbonylation reactions, in general, the use of supported ligands and anion exchange resins offer no advantage in the vapor phase carbonylation of alcohols compared to the use of the carbon as a support for the active metal component.

Nickel on activated carbon has been studied as a heterogeneous catalyst for the halide-promoted vapor phase carbonylation of methanol, and increased rates are observed when hydrogen is added to the feed mixture. Relevant references to the nickel-on-carbon catalyst systems are provided by Fujimoto et al. In *Chemistry Letters* (1987) 895–898 and in *Journal of Catalysis*, 133 (1992) 370–382 and in the references contained therein. Liu et al., in *Ind. Eng. Chem. Res.*, 33 (1994) 488–492, report that tin enhances the activity of the nickel-on-carbon catalyst. Mueller et al., in U.S. Pat. No. 4,918,218, disclose the addition of palladium and optionally copper to supported nickel catalysts for the halide-promoted carbonylation of methanol. In general the rates of reaction provided by nickel-based catalysts are lower than those provided by the analogous rhodium-based catalysts when operated under similar conditions.

Other single metals supported on carbon have been reported by Fujimoto et al. in *Catalysis Letters*, 2 (1989) 145–148 to have limited activity in the halide-promoted vapor phase carbonylation of methanol. The most active of these metals is Sn. Following Sn in order of decreasing activity are Pb, Mn, Mo, Cu, Cd, Cr, Re, V, Se, W, Ge and Ga. None of these other single metal catalysts are nearly as active as those based on Rh, Ir, Ni or the catalyst of the present invention.

A number of solid materials have been reported to catalyze the carbonylation of methanol without the addition of the halide promoter. Gates et al., in *Journal of Molecular Catalysis*, 3 (1977/78) 1–9, describe a catalyst containing rhodium attached to polymer bound polychlorinatedthiophenol for the liquid phase carbonylation of methanol. Current, in European Patent Application EP 0 130 058 A1, describes the use of sulfided nickel containing optional molybdenum as a heterogeneous catalyst for the conversion of ethers, hydrogen and carbon monoxide into homologous esters and alcohols. Smith et al., in European Patent Application EP 0 596 632 A1, describe the use of mordenite zeolite containing Cu, Ni, Ir, Rh, or Co as catalysts for the halide-free carbonylation of alcohols. Feitler, in U.S. Pat. No. 4,612,387, describes the use of certain zeolites containing no transition metals as catalysts for the halide-free carbonylation of alcohols and other compounds in the vapor phase. Wegman, in U.S. Pat. No. 5,218,140, describes the use of polyoxometallate anions containing Fe, Ru, Os, Co, Rh, Ir, Ni, Pd or Pt as catalysts for the halide-free carbonylation of alcohols and other compounds in the vapor phase. Although alcohol carbonylation without the use of halide promoters is very desirable, none of these halide-free catalyst systems have rates comparable to those of catalysts promoted by halide.

SUMMARY OF THE INVENTION

This invention pertains to a vapor phase process for the preparation of acetic acid, methyl acetate or mixtures thereof by contacting methanol vapor with carbon monoxide in the presence of a catalyst comprising iridium and at least one second metal selected from ruthenium, molybdenum, tungsten, palladium, platinum and rhenium deposited on a catalyst support material. Operation in the vapor phase distinguishes the present process from most of the prior art pertaining to methanol carbonylation wherein the reaction is carried out in the liquid phase utilizing a dissolved (homogeneous) catalyst.

The present invention provides a process for the preparation of acetic acid, methyl acetate or a mixture thereof which comprises the steps of:
(1) feeding a gaseous mixture comprising methanol, carbon monoxide, and a halide selected from chlorine, bromine, iodine and compounds thereof to a carbonylation zone which (i) contains a supported catalyst comprising iridium and at least one second metal selected from ruthenium, molybdenum, tungsten, palladium, platinum and rhenium deposited on a catalyst support material and (ii) is maintained under carbonylation conditions of temperature and pressure; and
(2) recovering a gaseous product comprising acetic acid, methyl acetate or a mixture thereof from the carbonylation zone.

Our novel heterogeneous process operates entirely in the gas phase, i.e., none of the compounds or materials present in the carbonylation zone or reactor exists in a mobile liquid phase. Several unique advantages are bestowed by operating in this mode. The following are some of the advantages provided by operating with a heterogeneous catalyst in the vapor phase as compared to the operation of existing commercial, liquid phase, homogenous processes:
(1) Elimination of the difficult and costly separation of catalyst materials from the liquid product obtained from homogeneous processes.
(b 2) Removal of the rate limitations imposed by mass transfer of carbon monoxide into the reaction medium which pose an ultimate ceiling on the achievable rates in the liquid phase, homogeneous process. Avoiding such rate limitation allows greatly enhanced reaction rates to be achieved in gas phase operation.
(3) Operation at a much lower pressure, permitting the use of lower cost materials in plant construction.

In addition, iodine-containing materials are less corrosive in the vapor phase permitting the possible use of lower cost metallurgies.

Compared to the majority of prior art, heterogeneous processes which operate under conditions in which the reactants and/or products are present as liquids, the process of the present invention, by operating entirely in the vapor phase, eliminates catalyst dissolution (leaching from the catalyst support), which occurs in the known heterogeneous processes operating in the presence of liquid components. Furthermore, the known operations in the presence of liquids are subject to the same problems associated with mass transfer of CO into a liquid reaction medium and the same upper limits associated with the homogeneous processes are observed. The process of the present invention provides faster rates and at lower pressures as a consequence of operating with a very active catalyst in the vapor phase. Lastly, when compared to the known, rhodium-catalyzed, vapor phase processes, which represent the best operation known to date, the catalyst used in our novel process is considerably less expensive, yet performs at a comparable rate.

DESCRIPTION OF THE INVENTION

The catalyst for the process of the invention comprises a mixture of iridium and at least one second metal selected from ruthenium, molybdenum, tungsten, palladium, platinum and rhenium deposited on a catalyst support material. Examples of potentially useful support materials include carbon and the oxides or mixed oxides of silicon, aluminum, zinc, zirconium, or titanium. The preferred support materials are selected from the wide variety of carbon, activated carbon, and silicon oxide sources available commercially. Oxides of aluminum, or materials containing oxides of aluminum are least preferred.

Typically, the catalyst is prepared by (1) dissolving soluble compounds of iridium and the second metal (or metals) in an appropriate solvent; (2) combining the solution of step (1) with the support material; (3) slowly evaporating the solvent; and, optionally, (4) heating the dried catalyst from step (3) at elevated temperature in a stream of inert gas or in a vacuum. Variations in this method of catalyst preparation are well known to those skilled in the art and may be used.

The compound or form of iridium used to prepare the catalyst generally is not critical, and the catalyst may be prepared from any of a wide variety of iridium containing compounds. Indeed, iridium compounds containing myriad combinations of halide, trivalent nitrogen, organic compounds of trivalent phosphorous, carbon monoxide, hydrogen, and 2,4-pentanedione, either alone or in combination, are available commercially and may be used in the preparation of the catalysts utilized in the present invention. In addition, the oxides of iridium may be used if dissolved in the appropriate medium. Based on their availability, cost, and high solubility in water (the preferred solvent medium) the preferred sources of iridium is one of it chlorides, such as the hydrated trichloride and any of the various salts of hexachloroiridate(IV). Use of either iridium trichloride or the hexacholoroiridate complexes should be comparable on the basis of cost, solubility, and performance.

Likewise, the compound or form of the second metal compound used to prepare the catalyst generally is not critical, and the catalyst may be prepared using any of a wide variety of compounds containing ruthenium, molybdenum, tungsten, palladium, platinum or rhenium. A wide variety of compounds of these elements containing various combinations of halides, acetates, nitrates, trivalent nitrogen, organic compounds of trivalent phosphorous, carbon monoxide, hydrogen, and 2,4-pentanedione, either alone or in combination, are available commercially and may be used in the preparation of the catalysts utilized in the present invention. In addition, the oxides of these materials may be used if dissolved in the appropriate medium. However, the compound used to provide the second metal preferably is a water soluble form of the metal(s). Based on their availability and cost, the preferred sources are the various acetates, nitrates, and halides of the second metals. The most preferred source among these salts would be dictated by its solubility (preferably water solubility) which can vary widely across this list of useful second components. For example, for the most preferred second promoters (Ru and Pd) the halides are generally available and quite soluble.

The content of iridium and the second component present on the catalysts can vary over a wide range, for example from about 0.01 to 10 weight percent for each metal. However, the preferred catalysts contain about 0.1 to 2 weight percent of each component. The second metal component of the catalysts utilized in the present invention preferably is ruthenium or molybdenum. The supported carbonylation catalysts which are particularly preferred comprise (i) iridium and ruthenium or (ii) iridium and molybdenum deposited on a catalyst support material selected from carbon, activated carbon, and silicon oxide wherein the iridium and ruthenium each constitute about 0.1 to 2 weight percent of the weight of the catalyst.

Although the methanol utilized in the process normally is fed as methanol, it can be supplied in the form of a combination of materials which generate methanol reactant. Examples of such combination of materials include (i) methyl acetate and water and (ii) dimethyl ether and water. In the operation of the process, both methyl acetate and dimethyl ether are formed within the reactor and, unless methyl acetate is the desired product, they are recycled with water to the reactor where they are later consumed to form acetic acid.

Although the presence of water in the gaseous feed mixture is not essential when using methanol, the presence of some water is desirable to suppress formation of methyl acetate and/or dimethyl ether. When using methanol to generate acetic acid, the molar ratio of water to methanol can be 0:1 to 10:1, but preferably is in the range of 0.01:1 to 1:1. When using an alternative source of methanol such as methyl acetate or dimethyl ether, the amount of water fed usually is increased to account for the mole of water required for hydrolysis of the methanol alternative. Therefore, when using either methyl acetate or dimethyl ether, the mole ratio of water to ester or ether is in the range of 1:1 to 10:1, but preferably in the range of 1:1 to 3:1. In the preparation of acetic acid, it is apparent that combinations of methanol, methyl ester, and/or dimethyl ether are equivalent, provided the appropriate amount of water is added to hydrolyze the ether or ester to provide the methanol reactant.

When the process is operated to produce methyl acetate, no water should be added and dimethyl ether becomes the preferred feedstock. Further, when methanol is used as the feedstock in the preparation of methyl acetate, it is necessary to remove water. However, the primary utility of the process of the present invention is in the manufacture of acetic acid.

The gaseous mixture fed to the carbonylation zone also contains a halide component selected from chlorine, bromine, iodine and compounds thereof. The preferred halide components are selected from bromine, bromine compounds and, especially, iodine and iodine compounds which are gaseous under the carbonylation conditions of temperature and pressure. The halide components may be fed in various forms although the preferred forms are as an alkyl halide, especially as methyl halide, the hydrogen halide, or as the molecular halide, i.e., $I_2$, $Br_2$, or $Cl_2$. The molar ratio of methanol (or methanol equivalents) to halide or halide compound may vary substantially but typically is in the range of 1:1 to 10,000:1, with the preferred range being between about 5:1 and 1000:1.

The carbon monoxide may be fed to the carbonylation zone either as purified carbon monoxide or as a mixture of hydrogen and carbon monoxide. Although a small quantity of hydrogen may be useful in maintaining optimal catalyst activity, e.g., CO:hydrogen volume ratios of 99.5:0.5 to 95:5, the ratio of carbon monoxide to hydrogen, the presence of hydrogen, is believed to be of only minor importance. Thus, CO:hydrogen ratios of 100:0 to 25:75 all seem to be useful. However, the preferred CO:hydrogen ratios normally are in the range of 99:1 to 2:1.

The process of this invention is operated in the vapor phase and, therefore, is practiced at temperatures above the dew point of the product mixture, i.e., the temperature at which condensation occurs. However, since the dew point is a complex function of dilution (particularly with respect to non-condensable gases such as unreacted carbon monoxide, hydrogen, or inert diluent gas), product composition, and pressure, the process may still be operated over a wide range of temperatures, provided the temperature exceeds the dew point of the product effluent. In practice, this generally dictates a temperature range of about 100 to 350° C., with temperatures in the range of 150 to 275° C. being particularly useful.

As with temperature, the useful pressure range is limited by the dew point of the product mixture. However, provided that the reaction is operated at a temperature sufficient to prevent liquefaction of the product effluent, a wide range of pressures may be used, e.g., pressures in the range of about 0.1 to 100 bars absolute (bara). The process preferably is carried out at a pressure in the range of about 1 to 50 bara, most preferably, about 3 to 30 bara.

EXAMPLES

The process of the present invention and the catalysts utilized in the process are further illustrated by the following examples.

PREPARATION OF CATALYSTS

CATALYST EXAMPLE 1

Iridium trichloride hydrate (418.9 mg) and ruthenium trichloride hydrate (275.7 mg) were dissolved in deionized water (30 mL). This mixture was added to 12×40 mesh activated carbon granules (20.0 g) having a BET surface area in excess of 800 m$^2$/g contained in an evaporating dish. The mixture was heated on the steam bath with occasional stirring until it became free flowing and then transferred to a quartz tube measuring 106 cm long by 25 mm outer diameter. The quartz tube containing the mixture was placed in a three-element electric tube furnace so that the mixture was located in the approximate center of the 61 cm long heated zone of the furnace. Nitrogen (100 standard cubic centimeters per minute) was continuously passed through the catalyst bed, and the tube was heated from ambient temperature to 300° C. over a 2 hour period, held at 300° C. for 2 hours and then allowed to cool back to ambient temperature. The catalyst prepared in this manner (Catalyst I) contained 1.00 weight percent Ir and 0.49 weight percent Ru and had a density of 0.57 g per mL.

The preceding procedure was repeated three times: first, to prepare a catalyst containing only iridium as the active metal (Comparative Catalyst C-I); second, to prepare a catalyst containing only ruthenium (Comparative Catalyst C-II); and third, by substituting 303.5 mg (1.166 mmol) of rhodium trichloride trihydrate for the iridium trichloride hydrate, to prepare a catalyst containing rhodium and ruthenium (Comparative Catalyst C-III).

CATALYST EXAMPLE 2

The procedure described in Example 1 was repeated except that 206.7 mg (1.166 mmol) of palladium chloride was substituted for the ruthenium trichloride hydrate to obtain a catalyst (Catalyst II) which contained 1.00 weight percent Ir and 0.49 weight percent Pd and had a density of 0.57 g per mL.

The procedure of Catalyst Example 2 was repeated twice: once, to prepare a catalyst containing only palladium as the active metal (Comparative Catalyst C-IV); and second, by substituting 303.5 mg (1.166 mmol) of rhodium trichloride trihydrate for the iridium trichloride hydrate, to prepare a catalyst containing rhodium and palladium (Comparative Catalyst C-V).

CATALYST EXAMPLE 3

The procedure described in Example 1 was repeated except that 312.7 mg (1.166 mmol) of ammonium perrhenate (NH$_4$ReO$_4$) was substituted for the ruthenium trichloride hydrate to obtain a catalyst (Catalyst III) which contained 1.00 weight percent Ir and 0.49 weight percent Re and had a density of 0.57 g per mL.

CATALYST EXAMPLE 4

The procedure described in Example 1 was repeated except that 20 g of silica gel (Davison Chemical Company, Baltimore, Md, Grade 57, mesh 8) was substituted for carbon during catalyst preparation to produce a catalyst comprising 1.00 weight percent Ir and 0.49 weight percent Ru on silica (Catalyst IV).

CATALYST EXAMPLE 5

The procedure described in Example 1 was repeated except that 331.06 mg (1.166 mmol of tungsten) of ammonium tungsten oxide [(NH$_4$)$_6$W$_{12}$O$_{41}$]·5 H$_2$O] was substituted for the ruthenium trichloride hydrate to obtain a catalyst (Catalyst V) which contained 1.08 weight percent Ir and 1.03 weight percent tungsten on activated carbon.

CATALYST EXAMPLE 6

The procedure described in Example 1 was repeated except that 205.85 mg (1.166 mmol of molybdenum) of ammonium molybdenum oxide [(NH$_4$)6Mo$_7$O$_{24}$)·5 H$_2$O] was substituted for the ruthenium trichloride hydrate to obtain a catalyst (Catalyst VI) which contained 1.05 weight percent Ir and 0.52 weight percent molybdenum on activated carbon.

COMPARATIVE CATALYST EXAMPLE C-6

The procedure described in Example 1 was repeated except that 1.153 g (4.665 mmol) of chromium acetate monohydrate was substituted for the ruthenium trichloride hydrate to obtain a catalyst (Comparative Catalyst C-VI) which contained 1.09 weight percent Ir and 0.29 weight percent chromium on activated carbon.

COMPARATIVE CATALYST EXAMPLE C-7

The procedure described in Example 1 was repeated except that 290.4 mg (1.166 mmol) of cobalt acetate tetrahydrate was substituted for the ruthenium trichloride hydrate to obtain a catalyst (Comparative Catalyst C-VII) which contained 1.08 weight percent Ir and 0.33 weight percent cobalt on activated carbon.

COMPARATIVE CATALYST EXAMPLE C-8

The procedure described in Example 1 was repeated except that 106.46 mg (1.166 mmol) of ferrous chloride was substituted for the ruthenium trichloride hydrate to obtain a catalyst (Comparative Catalyst C-VIII) which contained 1.09 weight percent Ir and 0.32 weight percent iron on activated carbon.

CARBONYLATION OF METHANOL

The reactor system consisted of a 800 to 950 mm (31.5 and 37 inch) section of 6.35 mm (¼ inch) diameter tubing constructed of Hastelloy alloy. The upper portion of the tube constituted the preheat and reaction (carbonylation) zones which were assembled by inserting a quartz wool pad 410 mm from the top of the reactor to act as support for the catalyst, followed sequentially by (1) a 0.7 g bed of fine quartz chips (840 microns), (2) 0.5 g of one of the catalysts prepared as described in the preceding examples, and (3) an additional 6 g of fine quartz chips. The top of the tube was attached to an inlet manifold for introducing liquid and gaseous feeds.

The six g of fine quartz chips acted as a heat exchange surface to vaporize the liquid feeds. Care was taken not to allow any liquid feeds to contact the catalyst bed at any time, including assembly, start-up, operation, and shutdown. The remaining lower length of tubing (product recovery section) consisted of a vortex cooler which varied in length depending on the original length of tubing employed and was maintained at approximately 0–5° C. during operation.

The gases were fed using Brooks flow controllers and liquids were fed using a high performance liquid chromatography pump. The gaseous products leaving the reaction zone were condensed using a vortex cooler operating at 0–5° C. The product reservoir was a tank placed downstream from the reactor system. The pressure was maintained using a modified Research control valve on the outlet side of the reactor system and the temperature of the reaction section was maintained using heating tape on the outside of the reaction system.

Feeding of hydrogen and carbon monoxide to the reactor was commenced while maintaining the reactor at a temperature of 240° C. and a pressure of 17.2 bara (250 psia). The flow rate of hydrogen was set at 25 standard cubic cm. per minute (cc/min) and the carbon monoxide flow rate was set at 100 cc/min. The reactor section was maintained under these conditions for 1 hour or until the temperature and pressure had stabilized (whichever was longer.) The high pressure liquid chromatography pump was then started, feeding a mixture consisting of 70 weight percent methanol and 30 weight percent methyl iodide at a rate of 10–12 g per hour. Samples of the liquid product were collected and analyzed periodically using gas chromatographic techniques.

CARBONYLATION EXAMPLE 1

The composition and weight of the samples taken periodically during the procedure described above in which Catalyst I was used are set forth in Table I wherein "Time" is the total time of operation (in hours) of the carbonylation commencing with the feeding of the methanol until a particular sample was taken. The values set forth below "MeI" (methyl iodide), "MeOAc"(methyl acetate), "MeOH" (methanol) and "HOAC" (acetic acid) are the weight percentages of each of those compounds present in the sample. The weight of each sample is given in grams.

TABLE I

| Sample Number | Time | MeI | MeOAc | MeOH | HOAc | Sample Weight |
|---|---|---|---|---|---|---|
| 1 | 3 | 22.11 | 26.97 | 28.03 | 5.57 | 33.5 |
| 2 | 5.5 | 22.34 | 27.58 | 27.74 | 6.45 | 33.3 |
| 3 | 7.5 | 21.86 | 28.89 | 27.31 | 6.93 | 20.1 |
| 4 | 10 | 23.0 | 31.22 | 24.65 | 8.0 | 33.5 |
| 5 | 13 | 22.74 | 31.08 | 22.56 | 9.18 | 52.7 |
| 6 | 15.5 | 21.71 | 28.83 | 26.18 | 7.27 | 31.1 |
| 7 | 19 | 22.48 | 31.66 | 24.29 | 8.61 | 42.7 |
| 8 | 22 | 21.6 | 35.2 | 12.44 | 14.57 | 34.9 |

TABLE I-continued

| Sample Number | Time | MeI | MeOAc | MeOH | HOAc | Sample Weight |
|---|---|---|---|---|---|---|
| 9 | 25.5 | 22.36 | 36.13 | 13.59 | 13.51 | 45.5 |
| 10 | 27 | 21.12 | 39.93 | 14.85 | 12.89 | 18.6 |

The rate of acetyl production based on the preceding experiment utilizing Catalyst I is set forth in Table II wherein Sample Number and Time values correspond to those of Table I. "Acetyl Produced" is the amount (millimoles) of methyl acetate and acetic acid produced during each increment of Time calculated from the formula:

$$\text{Sample Weight} \times 10 \times \frac{\text{Weight\% MeOAc}}{74} + \frac{\text{Weight\% AcOH}}{60}$$

"Production Rate" is the moles of Acetyl Produced per liter of catalyst volume per hour during each increment of Time (Time Increment), i.e., the time of operation between samples. The formula for determining moles of Acetyl Produced per liter of catalyst volume per hour is:

$$\frac{\text{Acetyl Produced}}{0.5 \times \text{Time Increment}} \times 0.57$$

wherein 0.5 is the grams of catalyst used and 0.57 is the density of the catalyst in g/mL.

TABLE II

| Sample Number | Time | Acetyl Produced | Production Rate |
|---|---|---|---|
| 1 | 3 | 153.2 | 58.2 |
| 2 | 5.5 | 159.9 | 72.9 |
| 3 | 7.5 | 101.7 | 58.0 |
| 4 | 10 | 186.0 | 84.8 |
| 5 | 13 | 302.0 | 114.7 |
| 6 | 15.5 | 158.8 | 72.4 |
| 7 | 19 | 244.0 | 79.5 |
| 8 | 22 | 250.8 | 95.3 |
| 9 | 25.5 | 324.6 | 105.7 |
| 10 | 27 | 140.4 | 106.7 |

Repetition of the above catalyst preparation and carbonylation procedures demonstrated a period of 3–8 hours during which the reaction rate continued to increase significantly (an induction period). After completion of the induction period, acetyl production rates averaged 90 moles/L-hour for 4 separate carbonylation experiments. The average acetyl production rate for the carbonylation experiment described herein was 94 moles/L-hour after the induction period.

CARBONYLATION EXAMPLES 2–6 AND COMPARATIVE CARBONYLATION

EXAMPLES C-1 –C-9

Catalysts II–VI and Comparative Catalysts C-I–C-IX were utilized in the carbonylation of methanol according to the above-described procedure. The Production Rate, i.e., the moles of Acetyl Produced per liter of catalyst volume per hour, provided by each of Catalysts II–VI and Comparative Catalysts C-I–C-IX is shown in Table III.

TABLE III

| Carbonylation Example | Catalyst | Production Rate |
| --- | --- | --- |
| C-1 | C-I | 52 |
| C-2 | C-II | 20 |
| C-3 | C-III | 34 |
| 2 | II | 86 |
| C-4 | C-IV | 2 |
| C-5 | C-V | 61 |
| 3 | III | 82 |
| 4 | IV | 81 |
| 5 | V | 93 |
| 6 | VI | 123 |
| C-6 | C-VI | 4 |
| C-7 | C-VII | 40 |
| C-8 | C-VIII | 3 |

The invention has been described in detail with particular reference to preferred embodiments thereof, but it will be understood that variations and modifications can be effected within the spirit and scope of the invention. CLAIMS

We claim:

1. Process for the preparation of acetic acid, methyl acetate or a mixture thereof which comprises the steps of:
   (1) feeding a gaseous mixture comprising methanol, carbon monoxide, and a halide selected from chlorine, bromine, iodine and compounds thereof to a carbonylation zone which (i) contains a supported catalyst comprising iridium and at least one second metal selected from ruthenium, molybdenum, tungsten, palladium, platinum and rhenium deposited on a catalyst support material and (ii) is maintained under carbonylation conditions of temperature and pressure; and
   (2) recovering a gaseous product comprising acetic acid, methyl acetate or a mixture thereof from the carbonylation zone;
   wherein none of the compounds present in the carbonylation zone exists in a mobile liquid phase.

2. Process according to claim 1 wherein the halide is selected from iodine, hydrogen iodide and methyl iodide and the carbonylation zone is maintained at a temperature of about 100 to 350° C. and a pressure of about 1 to 50 bar absolute.

3. Process according to claim 2 wherein the gaseous mixture includes water in an amount which gives a water::methanol mole ratio of about 0.01:1 to 1:1.

4. Process according to claim 1 wherein the catalyst comprises about 0.1 to 2 weight percent each of iridium and the second metal and the catalyst support material is selected from carbon, activated carbon, and silicon oxide.

5. Process for the preparation of acetic acid, methyl acetate or a mixture thereof which comprises the steps of:
   (1) feeding a gaseous mixture comprising methanol, carbon monoxide, and a halide selected from chlorine, bromine, iodine and compounds thereof to a carbonylation zone which (i) contains a supported catalyst comprising iridium, ruthenium and a catalyst support material and (ii) is maintained under carbonylation conditions of temperature and pressure; and
   (2) recovering a gaseous product comprising acetic acid, methyl acetate or a mixture thereof from the carbonylation zone;
   wherein none of the compounds present in the carbonylation zone exists in a mobile liquid phase.

6. Process according to claim 5 wherein the halide is selected from iodine, hydrogen iodide and methyl iodide and the carbonylation zone is maintained at a temperature of about 100 to 350° C. and a pressure of about 1 to 50 bar absolute.

7. Process according to claim 6 wherein the gaseous mixture includes water in an amount which gives a water::methanol mole ratio of about 0.01:1 to 1:1.

8. Process according to claim 5 wherein the catalyst comprises about 0.1 to 2 weight percent each of iridium and ruthenium and the catalyst support material is selected from carbon, activated carbon, and silicon oxide.

9. Process for the preparation of acetic acid which comprises the steps of:
   (1) feeding a gaseous mixture comprising methanol, water, carbon monoxide, and a halide selected from iodine, hydrogen iodide and methyl iodide to a carbonylation zone which (i) contains a supported catalyst comprising iridium, ruthenium and a catalyst support material selected from carbon, activated carbon, and silicon oxide and (ii) is maintained at a temperature of about 150 to 275° C. and a pressure of about 3 to 50 bar absolute; and
   (2) recovering a gaseous product comprising acetic acid from the carbonylation zone;
   wherein none of the compounds present in the carbonylation zone exists in a mobile liquid phase.

10. Process according to claim 9 wherein the water::methanol mole ratio in the gaseous feed to the carbonylation zone is about 0.01:1 to 1:1 and the catalyst comprises about 0.1 to 2 weight percent each of iridium and ruthenium.

11. Process for the preparation of acetic acid, methyl acetate or a mixture there of which comprises the steps of:
   (1) feeding a gaseous mixture comprising methanol, carbon monoxide, and a halide selected from chlorine, bromine, iodine and compounds thereof to a carbonylation zone which (i) contains a supported catalyst comprising iridium, molybdenum and a catalyst support material and (ii) is maintained under carbonylation conditions of temperature and pressure; and
   (2) recovering a gaseous product comprising acetic acid, methyl acetate or a mixture thereof from the carbonylation zone;
   wherein none of the compounds present in the carbonylation zone exists in a mobile liquid phase.

12. Process according to claim 11 wherein the halide is selected from iodine, hydrogen iodide and methyl iodide and the carbonylation zone is maintained at a temperature of about 100 to 350° C. and a pressure of about 1 to 50 bar absolute.

13. Process according to claim 12 wherein the gaseous mixture includes water in an amount which gives a water::methanol mole ratio of about 0.01:1 to 1:1.

14. Process according to claim 11 wherein the catalyst comprises about 0.1 to 2 weight percent each of iridium and molybdenum and the catalyst support material is selected from carbon, activated carbon, and silicon oxide.

15. Process for the preparation of acetic acid which comprises the steps of:
   (1) feeding a gaseous mixture comprising methanol, water, carbon monoxide, and a halide selected from iodine, hydrogen iodide and methyl iodide to a carbonylation zone which (i) contains a supported catalyst comprising iridium, molybdenum and a catalyst support material selected from carbon, activated carbon, and silicon oxide and (ii) is maintained at a temperature of about 150 to 275° C. and a pressure of about 3 to 50 bar absolute; and (2) recovering a gaseous product comprising acetic acid from the carbonylation zone;

wherein none of the compounds present in the carbonylation zone exists in a mobile liquid phase.

16. Process according to claim 15 wherein the water:methanol mole ratio in the gaseous feed to the carbonylation zone is about 0.01:1 to 1:1 and the catalyst comprises about 0.1 to 2 weight percent each of iridium and molybdenum.

* * * * *